United States Patent
Bhavsar et al.

(10) Patent No.: US 10,167,271 B2
(45) Date of Patent: Jan. 1, 2019

(54) FLUOROQUINOLONE CARBOXYLIC ACID COMPOUNDS AND USE THEREOF FOR THE PREPARATION OF BESIFLOXACIN HYDROCHLORIDE

(71) Applicant: MANKIND PHARMA LTD, New Delhi (IN)

(72) Inventors: Jigar Bhavsar, Haryana (IN); Bhuwan Bhashkar, Haryana (IN); Anil Kumar, Haryana (IN)

(73) Assignee: MANKIND PHARMA LTD (IN)

( * ) Notice: Subject to any disclaimer, the term of this patent is extended or adjusted under 35 U.S.C. 154(b) by 0 days.

(21) Appl. No.: 15/543,073

(22) PCT Filed: Jan. 28, 2016

(86) PCT No.: PCT/IB2016/050419
§ 371 (c)(1),
(2) Date: Jul. 12, 2017

(87) PCT Pub. No.: WO2016/120813
PCT Pub. Date: Aug. 4, 2016

(65) Prior Publication Data
US 2017/0362197 A1    Dec. 21, 2017

(30) Foreign Application Priority Data

Jan. 28, 2015 (IN) .............................. 252/DEL/2015

(51) Int. Cl.
*A61K 31/55* (2006.01)
*C07D 401/04* (2006.01)

(52) U.S. Cl.
CPC .................... *C07D 401/04* (2013.01)

(58) Field of Classification Search
CPC ............................. A61K 31/55; C07D 401/04
USPC ...................... 514/217.07; 540/596
See application file for complete search history.

(56) References Cited

U.S. PATENT DOCUMENTS

2008/0176834 A1    7/2008    Harms
2012/0110701 A1    5/2012    Garizi et al.

OTHER PUBLICATIONS

Corresponding International Search Report and Written Opinion for PCT/IB2016/050419 dated Mar. 18, 2016. WO.
Noemi Cabello-Sanchez et al: "Palladium-Mediated N-Arylation of Heterocyclic Diamines: Insights into the Origin of an Unusual Chemoselectivity", The Jorunal of Organic Chemistry, vol. 72, No. 6, 2007, pp. 2030-2039, XP055259397 (Abstract). FR.

*Primary Examiner* — Brenda L Coleman
(74) *Attorney, Agent, or Firm* — Belles Katz LLC

(57) ABSTRACT

The present invention relates to novel fluoroquinolone carboxylic acid compounds and derivatives of Formula-I, and their salts wherein, R represents H or halogen. The present invention also relates to the use of novel fluoroquinolone carboxylic acid compounds and derivatives of Formula-I for preparation of Besifloxacin hydrochloride.

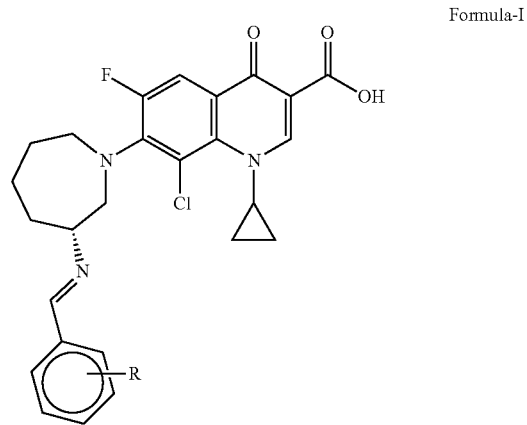

Formula-I

10 Claims, No Drawings

FLUOROQUINOLONE CARBOXYLIC ACID COMPOUNDS AND USE THEREOF FOR THE PREPARATION OF BESIFLOXACIN HYDROCHLORIDE

CROSS-REFERENCE TO RELATED APPLICATIONS

This application is a U.S. national stage application under 35 U.S.C. § 371 of PCT Application No. PCT/IB2016/050419, filed Jan. 28, 2016, which claims priority to Indian Patent Application No. 252/DEL/2015, filed Jan. 28, 2015, the entireties of which are incorporated herein by reference.

FIELD OF THE INVENTION

The present invention relates to novel fluoroquinolone carboxylic acid compounds, derivatives of Formula-I and their salts wherein, R represents H or halogen. The invention also relates to their use as intermediate for preparation of Besifloxacin or its salts, such as Besifloxacin hydrochloride wherein, said intermediate is optionally isolated.

The present invention further relates to an economical and industrially favorable process for the preparation of said intermediate wherein, the process may also be performed in single pot.

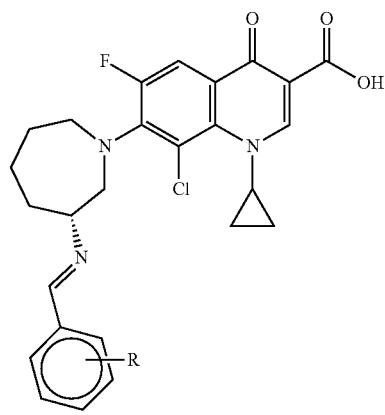

Formula-I

BACKGROUND AND PRIOR ART

The compound 7-[(3R)-3-aminohexahydro-1H-azepin-1-yl]-8-chloro-1-cyclopropyl-6-fluoro-1,4-dihydro-4-oxoquinoline-3-carboxylic acid and its hydrochloride salt generally known by name, Besifloxacin hydrochloride of Formula-II is an antibacterial agent and have activity against Gram-negative and Gram-positive bacteria.

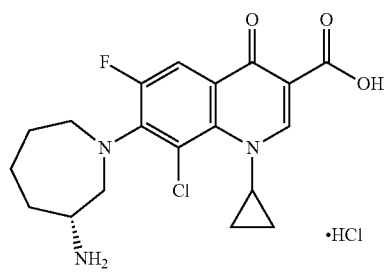

Formula-II

Besifloxacin hydrochloride of Formula-II is disclosed in U.S. Pat. No. 5,447,926 (U.S. Pat. No. '926). Preparative process described in this patent is carried out by: (a) reacting 1-cyclopropyl-6,7-difluoro-4-oxo-1,4-dihydroquinoline-3-carboxylic acid of Formula-III with (R)-azepan-3-amine of Formula-IV in acetonitrile followed by chlorination in presence of sulfuryl chloride to give Besifloxacin of Formula-VI, which is purified through column chromatography. The reaction sequence is shown in scheme-1.

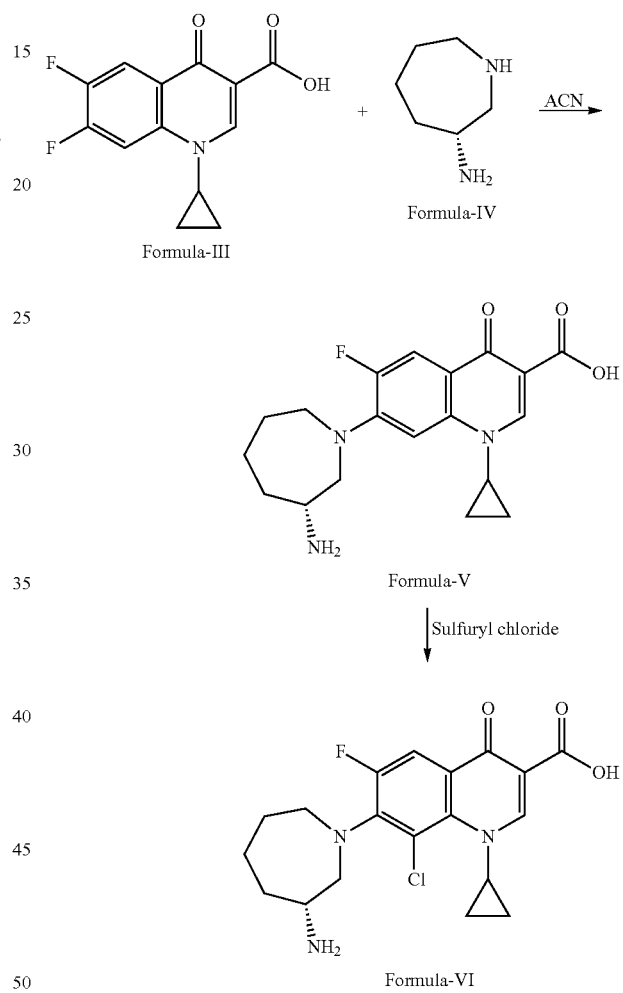

The major drawback of the above said process is poor yield and purity of Besifloxacin. The reaction method disclosed in U.S. Pat. No. '926; requires large time for completion, hence not suitable for plant scale production. Also use of column chromatography for purification purpose is neither economical nor environmental friendly, especially when performed at large scale.

PCT application no. WO2008/045673, describes process for preparation of Besifloxacin of Formula-VI which encompasses use of intermediate, 8-chloro-1-cyclopropyl-6-fluoro-7-(3-((3-nitrobenzylidene)amino)azepan-1-yl)-4-oxo-1,4-dihydroquinoline-3-carboxylic acid of Formula-IX as shown in Scheme-2.

Scheme-2

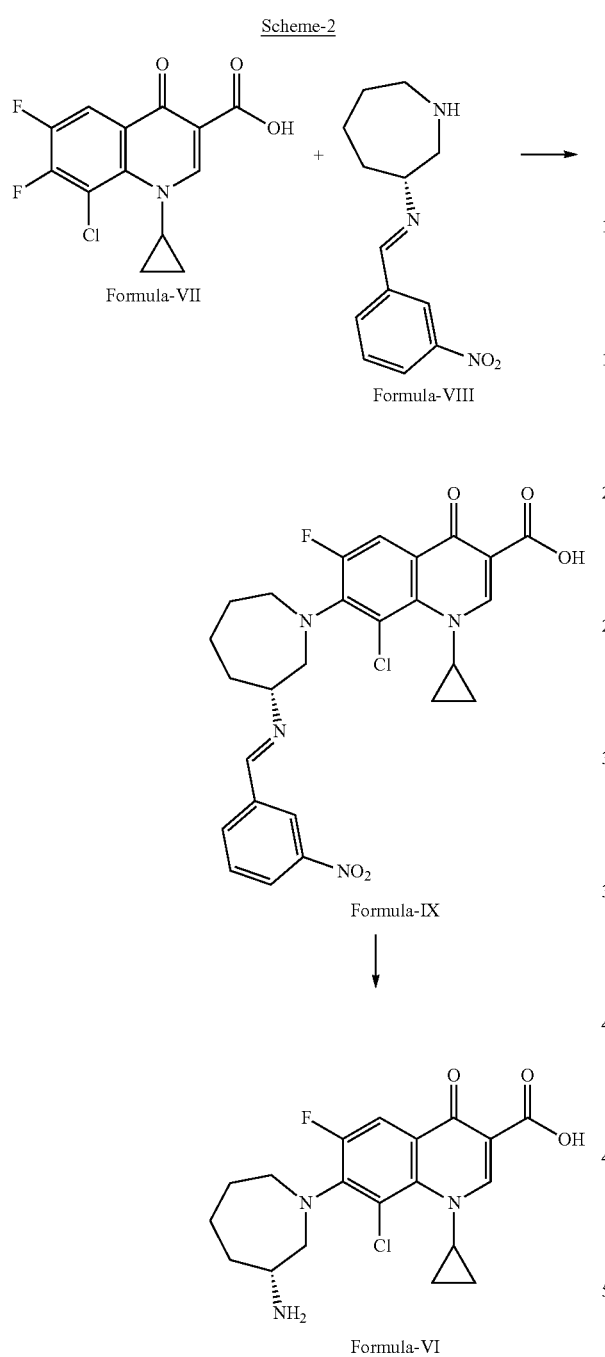

Scheme-3

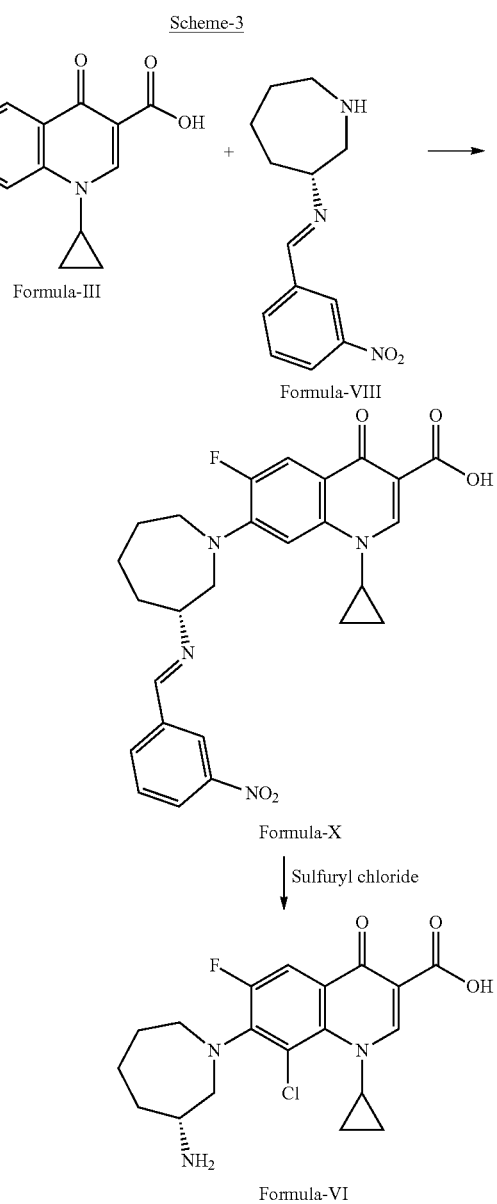

The major drawback of the above said process is use of side chain of Formula-VIII, which requires coupling of 3-amino azepane with nitro benzaldehyde. Nitro benzaldehyde is an expensive reagent and making of same is not a good option especially at large scale, as nitration in itself is a hazardous process and is unfriendly for human and environment.

US Patent application no. 2008/0176834, describes use of intermediate of Formula-X in preparation of Besifloxacin as shown in Scheme-3.

There are two major drawbacks in above said process such as use of a) expensive reagent of Formula-VIII and b) large volume of sulfuryl chloride, thereby making process highly uneconomical.

Therefore, there is a need to develop a new process for preparation of Besifloxacin hydrochloride in high yield that encompasses use of economic and environmental friendly reagents and intermediates.

The present inventors have worked on the development of new process for preparation of Besifloxacin hydrochloride through novel fluoroquinolone carboxylic acid intermediates prepared by the use of inexpensive, easily available, human as well as environmental friendly reagents.

OBJECT AND SUMMARY OF THE INVENTION

According to one aspect of the present invention, there are provided novel fluoroquinolone carboxylic acid compounds and derivatives of Formula-I and salts thereof;

Formula-I

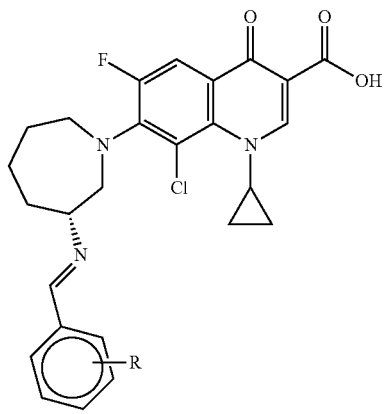

wherein, R represents hydrogen or halogen.

According to another aspect of the present invention, there are provided novel fluoroquinolone carboxylic acid compounds and derivatives of Formula I and salts thereof, wherein compounds of Formula I are selected from the following compounds:

Formula-A

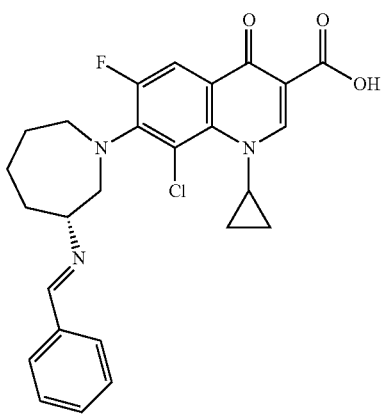

Formula-B

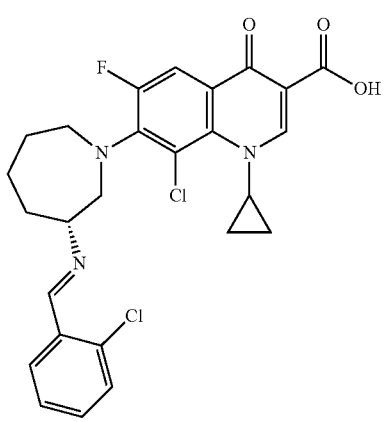

Formula-C

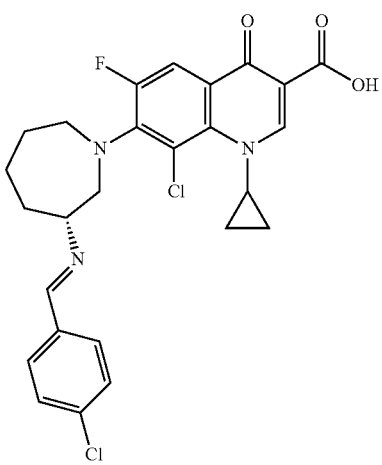

Formula-D

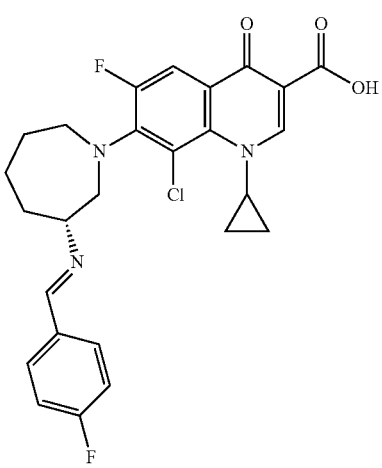

Formula-E

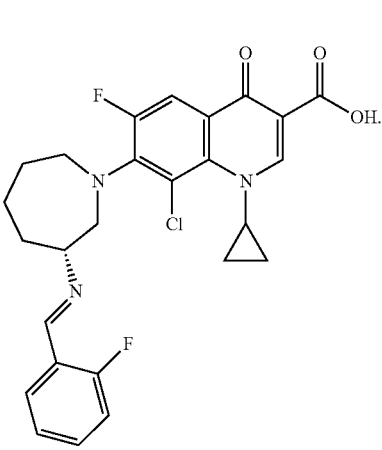

According to another aspect of the present invention, there is provided an economical, industrially viable and human friendly process for preparation of novel fluoroquinolone carboxylic acid compounds and derivatives of Formula-I which comprises of:

reaction of Schiff base of Formula-XIII with 8-chloro-1-cyclopropyl-6,7-difluoro-4-oxo-1,4-dihydroquinoline-3-carboxylic acid of Formula-VII;

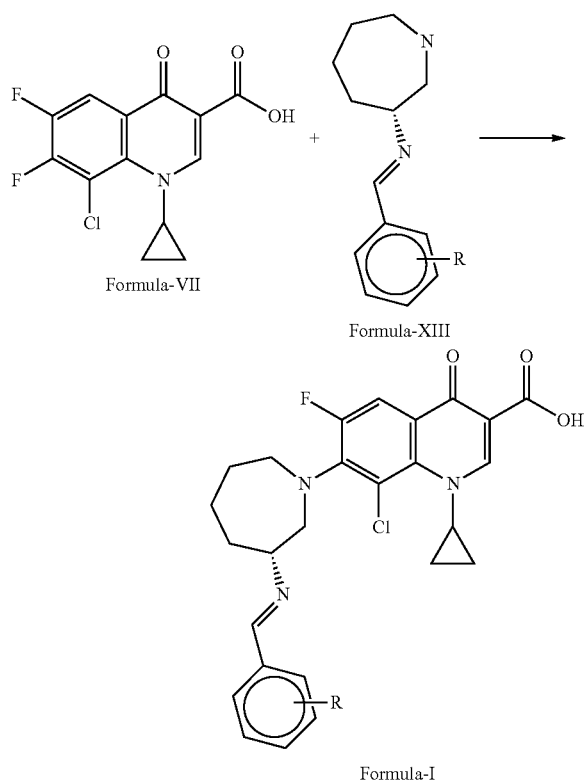

Formula-VII

Formula-XIII

Formula-I wherein, above said Schiff base is prepared by reacting (R)-azepan-3-amine of Formula-XI with compound of Formula-XII;

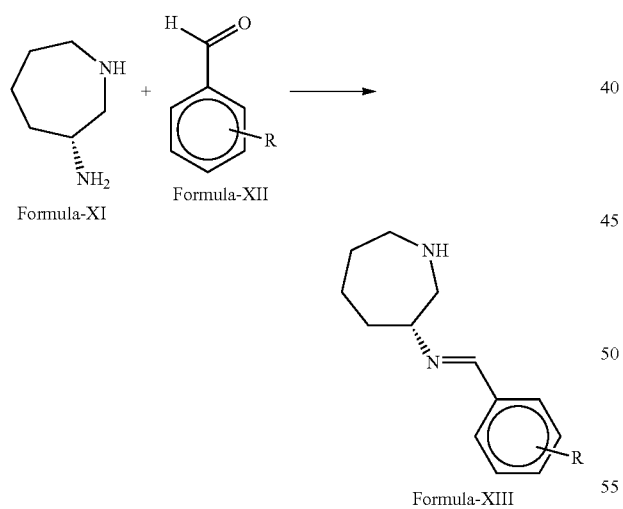

Formula-XI

Formula-XII

Formula-XIII where, R is as defined above.

According to further aspect of the present invention, there is provided the use of novel fluoroquinolone compounds and derivatives of Formula-I, and salts thereof, in preparation of Besifloxacin hydrochloride which comprises de-protection of compounds of Formula-I by addition of aqueous hydrochloric acid to give Besifloxacin hydrochloride.

To solve the above-mentioned object, the specific embodiment thereof will be described as per the annexed claims. While the invention will now be described in detail in connection with certain embodiments it is anticipated that the invention can be more clearly understood and appreciated. However, the described embodiments are in accordance with the best mode of practice and the scope of the invention is not restricted to the described embodiments herein after.

DETAILED DESCRIPTION OF THE INVENTION

Now the specification will be providing more details that are pertinent for understanding the embodiments of the present invention and so as not to obscure the disclosure with details that will be readily apparent to those of ordinary skill in the art having benefit of the description herein.

Further characteristics and advantages of the process according to the invention will result from the description herein below of preferred exemplary embodiments, which are given as indicative and non-limiting examples.

Definitions

The invention is described herein in detail using the terms defined below unless otherwise specified.

The term "halogen" includes fluorine, chlorine, iodine and bromine.

The term "salts" refers to non-toxic inorganic or organic acid salts. The salts may be prepared during isolation or purification of the compounds and derivatives. The salts includes but not limited to acetate, trifluoroacetate, oxalate, maleate, tartrate, methanesulfonate, formate, succinate, paratoluene sulphonate, glutamate, trichloroacetate, citrate, benzoate, fumarate, hydrochloride, hydrobromide, sulphate, nitrate, phosphate, and the like.

The term "derivatives" refers to a compound that is derived from a similar compound by a chemical reaction.

The term "in situ process" refers to within the reaction wherein, the compounds formed in the reaction are taken to the next step without isolation from the reaction mass.

The term "one pot process" refers to a strategy to improve the efficiency of a chemical reaction whereby a reactant is subjected to successive chemical reactions in just one reactor or one Round Bottom Flask (RBF).

In accordance with one embodiment of the present invention, there are provided novel fluoroquinolone carboxylic acid compounds and derivatives of Formula-I and salts thereof;

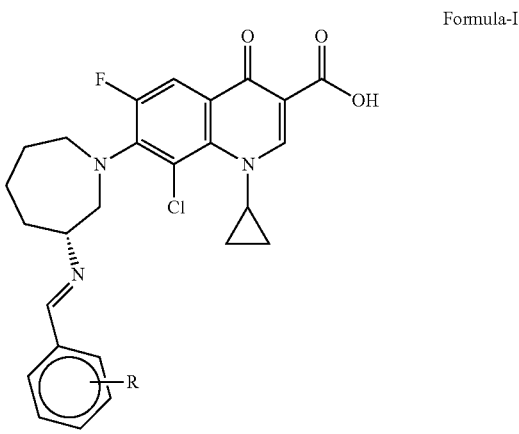

Formula-I wherein, R represents hydrogen or halogen.

In accordance to another embodiment of the present invention, there are provided novel fluoroquinolone carboxylic acid compounds and derivatives of Formula 1 and salts thereof wherein, compounds of Formula 1 are selected from;

Formula-A

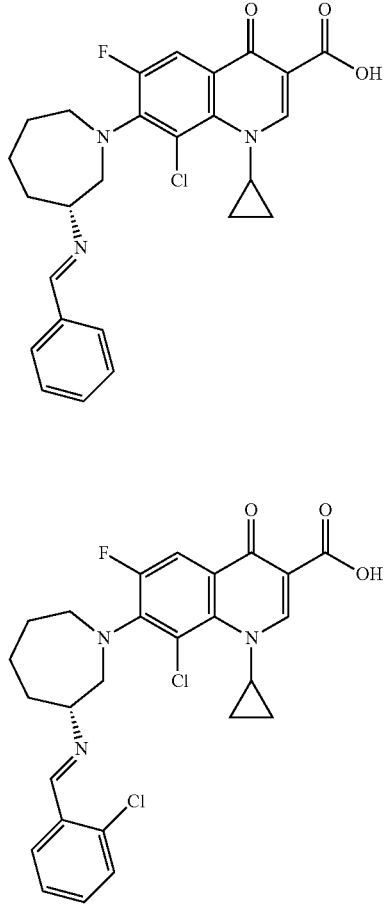

Formula-B

Formula-C

Formula-D

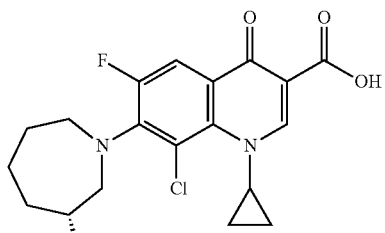

Formula-E

In accordance to another embodiment of the present invention, there is provided a process for preparation of novel fluoroquinolone carboxylic acid compounds and derivatives of Formula-I which comprises of:

reaction of Schiff base of Formula-XIII with 8-chloro-1-cyclopropyl-6,7-difluoro-4-oxo-1,4-dihydroquinoline-3-carboxylic acid of Formula-VII;

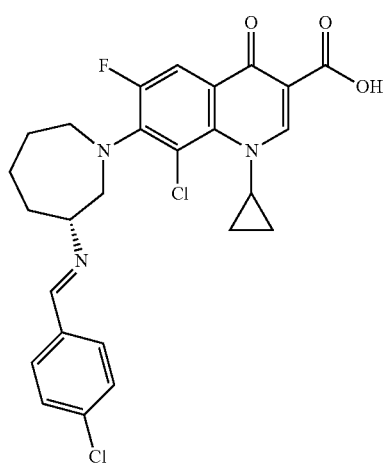

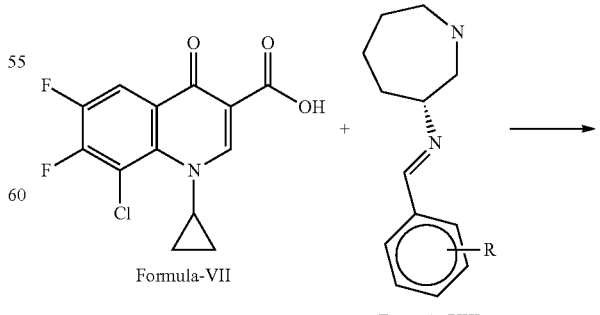

Formula-VII

Formula-XIII

-continued

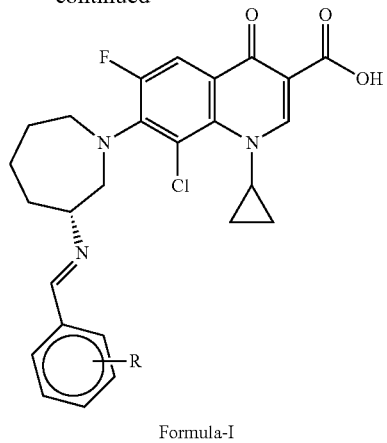

Formula-I where, R is as defined above.

In an embodiment of the present invention, Schiff base of Formula-XIII reacts with 8-chloro-1-cyclopropyl-6,7-difluoro-4-oxo-1,4-dihydroquinoline-3-carboxylic acid of Formula-VII at a temperature in the range of 60 to 90° C.

In a preferred embodiment of the above process, the said Schiff base is prepared by reacting (R)-azepan-3-amine of Formula-XI with compound of Formula-XII;

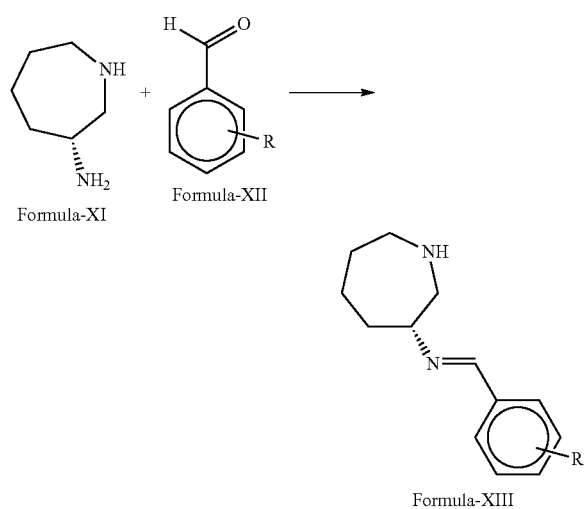

where, R is as defined above.

In an embodiment of the present invention, (R)-azepan-3-amine of Formula-XI reacts with compound of Formula-XII at a temperature in the range of 20 to 30° C.

In yet another embodiment of the present invention, the mole ratio of (R)-azepan-3-amine of Formula-XI with compound of Formula-XII is in the range of 1:1 to 1:2.

In accordance to still another embodiment of the present invention, compound of Formula-XII is a benzaldehyde optionally substituted with halogen like chloro, bromo, iodo and fluoro. The preferred structures of compounds of Formula-XII are benzaldehyde, o-chloro benzaldehyde and p-fluoro benzaldehyde.

In accordance to yet another embodiment of the present invention, the said Schiff base of Formula-XIII is an R-enantiomer.

In accordance to further embodiment of the present invention, the said process may be carried out either in a single pot or through in situ process, without isolation of Schiff base of Formula-XIII.

In accordance to yet further embodiment of the present invention, there is provided the use of novel fluoroquinolone compounds and derivatives of Formula-I, and salts thereof, in preparation of Besifloxacin hydrochloride.

In accordance to furthermore embodiment of the present invention, the fluoroquinolone compounds and derivatives of Formula-I, and salts thereof, can be used as intermediate in preparation of Besifloxacin hydrochloride wherein, the process comprises of de-protection of said fluoroquinolones in presence of aqueous hydrochloric acid.

It may be noted that it is possible to obtain Besifloxacin hydrochloride of Formula-II by following process:

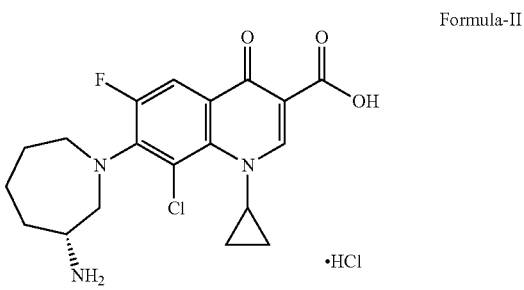 [SMILES: N[C@@H]1CCCCN(c2c(F)cc3c(=O)c(C(=O)O)cn(C4CC4)c3c2Cl)C1 ; Cl]

Formula-II a) The fluoroquinolone compounds and derivatives of Formula-I, can be prepared as per the process of the present invention wherein, the said process of preparation can be carried out in a single pot and the said fluoroquinolones so obtained can be in situ converted to Besifloxacin hydrochloride by addition of aqueous hydrochloric acid.

b) The fluoroquinolone compounds and derivatives of Formula-I, can be prepared as per the process of the present invention wherein, the said process of preparation can be carried out through in situ without isolation of intermediates, and the said fluoroquinolones so obtained are isolated in pure solid form followed by amine de-protection to give Besifloxacin hydrochloride in presence of aqueous hydrochloric acid.

In an embodiment of the present invention, fluoroquinolone compounds and derivatives of Formula-I reacts with aqueous hydrochloric acid at a temperature in the range of 20 to 80° C.

In an embodiment of the present invention, fluoroquinolone compounds and derivatives of Formula-I react with aqueous hydrochloric acid at pH in the range of 0.5 to 3.0.

Analytics and Instrumentation:

$^1$HNMR spectra were recorded on a Bruker Asend 500 spectrometer in $CDCl_3$ at 500 MHz using TMS as an internal standard. All chemical shifts were reported on δ scales.

LC-MS spectra were recorded on a MS Xevo TQD Waters LC-MS spectrometer.

Purity of compounds were analysed by High Performance Liquid Chromatography (HPLC) using Waters e2695 HPLC by conventional methods.

While specific embodiments of the present invention have been described in the foregoing, it will be appreciated by those skilled in the art that many equivalents, modifications, substitutions, and variations may be made thereto without departing from the spirit and scope of the invention as defined in the appended claims.

Example 1: In Situ Preparation of (R)-7-(3-(benzylideneamino)azepan-1-yl)-8-chloro-1-cyclopropyl-6-fluoro-4-oxo-1,4-dihydroquinoline-3-carboxylic Acid of Formula-I (R=H, Formula-A)

To a solution of 10 g (0.0877 mol) of (R)-azepan-3-amine in 50 ml of acetonitrile was added 13.9 g (0.13 mol) of benzaldehyde and 10 g of magnesium sulfate under stirring at room temperature. Stirred the reaction mass till formation of Schiff base, (R)—N-benzylideneazepan-3-amine. Filtered the suspension and to the mother liquor was added 22 g (0.0734 mol) of 8-chloro-1-cyclopropyl-6,7-difluoro-4-oxo-1,4-dihydroquinoline-3-carboxylic acid followed by slow addition of 8.9 g (0.088 mol) of triethyl amine. Heated the reaction mass at reflux temperature till completion of reaction. Distilled the acetonitrile to get the crude mass. Added hexane to the crude mass so obtained and stirred for 30 min at room temperature. Filtered the solid precipitates and washed with hexane. Dried the precipitates to get 29.3 g of pure (R)-7-(3-(benzylideneamino)azepan-1-yl)-8-chloro-1-cyclopropyl-6-fluoro-4-oxo-1,4-dihydroquinoline-3-carboxylic acid.
Purity (HPLC): 98%.
1HNMR: δ 8.89 (1H, s), 8.29 (1H, s), 7.67-7.55 (5H, m), 7.39 (1H, d), 4.35 (1H, m), 3.79-3.62 (2H, t), 3.43-3.18 (3H, m), 2.01-1.93 (6H, m), 1.31 (2H, m), 0.98-0.92 (2H, q).
m/z (M+1): 481.76

Example 2: One Pot Preparation of (R)-7-(3-(benzylideneamino)azepan-1-yl)-8-chloro-1-cyclopropyl-6-fluoro-4-oxo-1,4-dihydroquinoline-3-carboxylic Acid of Formula-I (R=H, Formula-A)

To a solution of 10 g (0.0877 mol) of (R)-azepan-3-amine in 50 ml of acetonitrile was added 13.9 g (0.13 mol) of benzaldehyde and 10 g of magnesium sulfate under stirring at room temperature. Stirred the reaction mass for 5 h and added 22 g (0.0734 mol) of 8-chloro-1-cyclopropyl-6,7-difluoro-4-oxo-1,4-dihydroquinoline-3-carboxylic acid followed by slow addition of 8.9 g (0.088 mol) of triethyl amine. Heated the reaction mass at reflux temperature till completion of reaction. Filtered the reaction mass and distilled the mother liquor to get crude mass. Added hexane to the crude mass so obtained and stirred for 30 min at room temperature. Filtered the solid precipitates and washed with hexane. Dried the precipitates to get 29.1 g of pure (R)-7-(3-(benzylideneamino)azepan-1-yl)-8-chloro-1-cyclopropyl-6-fluoro-4-oxo-1,4-dihydroquinoline-3-carboxylic acid.
Purity (HPLC): 96.5%.
1HNMR: 58.89 (1H, s), 8.29 (1H, s), 7.67-7.55 (5H, m), 7.39 (1H, d), 4.35 (1H, m), 3.79-3.62 (2H, t), 3.43-3.18 (3H, m), 2.01-1.93 (6H, m), 1.31 (2H, m), 0.98-0.92 (2H, q).
m/z (M+1): 481.76

Example 3: In Situ Preparation of (R)-7-(3-((2-chlorobenzylidene)amino)azepan-1-yl)-8-chloro-1-cyclopropyl-6-fluoro-4-oxo-1,4-dihydroquinoline-3-carboxylic Acid of Formula-I (R=ortho-Cl, Formula-B)

To a solution of 0.46 g (0.0040 mol) of (R)-azepan-3-amine in 5 ml of acetonitrile was added 0.85 g (0.006 mol) of ortho-chlorobenzaldehyde and 1 g of magnesium sulfate under stirring at room temperature. Stirred the reaction mass till formation of Schiff base, (R)—N-(2-chlorobenzylidene)azepan-3-amine. Filtered the suspension and to the mother liquor was added 1 g (0.0033 mol) of 8-chloro-1-cyclopropyl-6,7-difluoro-4-oxo-1,4-dihydroquinoline-3-carboxylic acid followed by slow addition of 0.40 g (0.0040 mol) of triethyl amine. Heated the reaction mass at reflux temperature till completion of reaction. Distilled the acetonitrile to get the crude mass. Added hexane to the crude mass so obtained and stirred for 20 min at room temperature. Filtered the solid precipitates and washed with hexane. Dried the precipitates to get 1.4 g of pure (R)-7-(3-((2-chlorobenzylidene)amino)azepan-1-yl)-8-chloro-1-cyclopropyl-6-fluoro-4-oxo-1,4-dihydroquinoline-3-carboxylic acid.
Purity (HPLC): 97%.
1HNMR: δ 8.91 (1H, s), 8.75 (1H, s), 8.024-7.93 (2H, d), 7.32-7.29 (2H, m), 7.24 (1H, d), 4.35 (1H, m), 3.78-3.69 (2H, t), 3.41-3.27 (3H, m), 2.02-1.81 (6H, m), 1.38-1.25 (2H, d), 1.06-0.92 (2H, q).
m/z (M+1): 515.94

Example 4: One Pot Preparation of (R)-7-(3-((4-fluorobenzylidene)amino)azepan-1-yl)-8-chloro-1-cyclopropyl-6-fluoro-4-oxo-1,4-dihydroquinoline-3-carboxylic Acid of Formula-I (R=para-F, Formula-D)

To a solution of 0.46 g (0.0040 mol) of (R)-azepan-3-amine in 5 ml of acetonitrile was added 0.75 g (0.006 mol) of para-fluorobenzaldehyde and 1 g of magnesium sulfate under stirring at room temperature. Stirred the reaction mass for 5 h and added 1 g (0.0033 mol) of 8-chloro-1-cyclopropyl-6,7-difluoro-4-oxo-1,4-dihydroquinoline-3-carboxylic acid followed by slow addition of 0.40 g (0.0040 mol) of triethyl amine. Heated the reaction mass at reflux temperature till completion of reaction. Filtered the reaction mass and distilled the mother liquor to get crude mass. Added isopropyl ether to the crude mass so obtained and stirred for 30 min at room temperature. Filtered the solid precipitates and washed with isopropyl ether. Dried the precipitates to get 1.33 g of pure (R)-7-(3-((4-fluorobenzylidene)amino)azepan-1-yl)-8-chloro-1-cyclopropyl-6-fluoro-4-oxo-1,4-dihydroquinoline-3-carboxylic acid
Purity (HPLC): 97.66%.
1HNMR: δ 8.87 (1H, s), 8.35 (1H, s), 7.98-7.96 (1H, d), 7.66-7.52 (2H, d), 7.057-7.041 (2H, d), 4.34 (1H, m), 3.83-3.70 (2H, t), 3.41-3.27 (3H, m), 2.00-1.78 (6H, m), 1.32-1.26 (2H, q), 0.99-0.92 (2H, q).
m/z (M+1): 499.98

Example 5: One Pot Preparation of (R)-7-(3-((2-chlorobenzylidene)amino)azepan-1-yl)-8-chloro-1-cyclopropyl-6-fluoro-4-oxo-1,4-dihydroquinoline-3-carboxylic Acid of Formula-I (R=ortho-Cl, Formula-B)

To a solution of 0.46 g (0.0040 mol) of (R)-azepan-3-amine in 5 ml of acetonitrile was added 0.75 g (0.006 mol) of ortho-chlorobenzaldehyde and 1 g of magnesium sulfate under stirring at room temperature. Stirred the reaction mass for 5 h and added 1 g (0.0033 mol) of 8-chloro-1-cyclopropyl-6,7-difluoro-4-oxo-1,4-dihydroquinoline-3-carboxylic acid followed by slow addition of 0.40 g (0.0040 mol) of triethylamine. Followed the procedure as disclosed in example 4 to get 1.4 g of (R)-7-(3-((2-chlorobenzylidene)amino)azepan-1-yl)-8-chloro-1-cyclopropyl-6-fluoro-4-oxo-1,4-dihydroquinoline-3-carboxylic acid.
Purity (HPLC): 95.77%.
1HNMR: δ 8.91 (1H, s), 8.75 (1H, s), 8.024-7.93 (2H, d), 7.32-7.29 (2H, m), 7.24 (1H, d), 4.35 (1H, m), 3.78-3.69 (2H, t), 3.41-3.27 (3H, m), 2.02-1.81 (6H, m), 1.38-1.25 (2H, d), 1.06-0.92 (2H, q).
m/z (M+1): 515.94

Example 6: In Situ Preparation of (R)-7-(3-((4-fluorobenzylidene)amino)azepan-1-yl)-8-chloro-1-cyclopropyl-6-fluoro-4-oxo-1,4-dihydroquinoline-3-carboxylic Acid of Formula-I (R=para-F, Formula-D)

To a solution of 0.46 g (0.0040 mol) of (R)-azepan-3-amine in 5 ml of acetonitrile was added 0.75 g (0.006 mol) of para-fluorobenzaldehyde and 1 g of magnesium sulfate under stirring at room temperature. Stirred the reaction mass till formation of Schiff base, (R)—N-(4-fluorobenzylidene)azepan-3-amine. Followed the procedure as disclosed in example 3 to get 1.3 g of (R)-7-(3-((4-fluorobenzylidene)amino)azepan-1-yl)-8-chloro-1-cyclopropyl-6-fluoro-4-oxo-1,4-dihydroquinoline-3-carboxylic acid.

Purity (HPLC): 97.5%.

1HNMR: δ 8.87 (1H, s), 8.35 (1H, s), 7.98-7.96 (1H, d), 7.66-7.52 (2H, d), 7.057-7.041 (2H, d), 4.34 (1H, m), 3.83-3.70 (2H, t), 3.41-3.27 (3H, m), 2.00-1.78 (6H, m), 1.32-1.26 (2H, q), 0.99-0.92 (2H, q).

m/z (M+1): 499.98

Example 7: Preparation of Besifloxacin Hydrochloride Using (R)-7-(3-(benzylideneamino)azepan-1-Yl)-8-chloro-1-cyclopropyl-6-fluoro-4-oxo-1,4-dihydroquinoline-3-carboxylic Acid of Formula-I (R=H, Formula-A) as an Intermediate To solution of 28.0 g of (R)-7-(3-(benzylideneamino)azepan-1-yl)-8-chloro-1-cyclopropyl-6-fluoro-4-oxo-1,4-dihydroquinoline-3-carboxylic acid in 50 ml of methanol added aqueous hydrochloric acid and 200 ml of acetone. Maintained the pH at 2.0 and stirred the reaction mass at room temperature for 30 min followed by filtration of precipitates. Washed the precipitates with acetone and water followed by drying to give 22 g of Besifloxacin hydrochloride.

Purity (HPLC): 99.3%.

Example 8: Preparation of Besifloxacin Hydrochloride without Isolation of Intermediate (R)-7-(3-(benzylideneamino)azepan-1-yl)-8-chloro-1-cyclopropyl-6-fluoro-4-oxo-1,4-dihydroquinoline-3-carboxylic Acid of Formula-I (R=H, Formula-A)

To a solution of 10 g (0.0877 mol) of (R)-azepan-3-amine in 50 ml of acetonitrile was added 13.9 g (0.13 mol) of benzaldehyde and 10 g of magnesium sulfate under stirring at room temperature. Stirred the reaction mass till formation of Schiff base, (R)—N-benzylideneazepan-3-amine. Filtered the suspension and to the mother liquor was added 22 g (0.0734 mol) of 8-chloro-1-cyclopropyl-6,7-difluoro-4-oxo-1,4-dihydroquinoline-3-carboxylic acid followed by slow addition of 8.9 g (0.088 mol) of triethyl amine. Heated the reaction mass at reflux temperature till completion of reaction. Distilled the acetonitrile and added 20 ml of methanol. Acidified the solution by addition of aqueous hydrochloric acid and 100 ml of acetone. Maintained the pH to 2.0 and stirred the reaction mass at room temperature for 30 min. Filtered the precipitates and washed with acetone and water. Dried the wet cake to get 23 g of Besifloxacin hydrochloride.

Purity (HPLC): 99.6%.

Example 9: Preparation of Besifloxacin Hydrochloride Using (R)-7-(3-((2-chlorobenzylidene)amino)azepan-1-yl)-8-chloro-1-cyclopropyl-6-fluoro-4-oxo-1,4-dihydroquinoline-3-carboxylic Acid of Formula-I (R=ortho-chloro, Formula-B) as an Intermediate Followed the procedure as disclosed in example 7 by using 1.4 g of (R)-7-(3-((2-chlorobenzylidene)amino)azepan-1-yl)-8-chloro-1-cyclopropyl-6-fluoro-4-oxo-1,4-dihydroquinoline-3-carboxylic acid to give 1.0 g of Besifloxacin hydrochloride.

Purity (HPLC): 99.68%.

The invention claimed is:

1. Fluoroquinolone carboxylic acid compounds of Formula-I, and salts thereof:

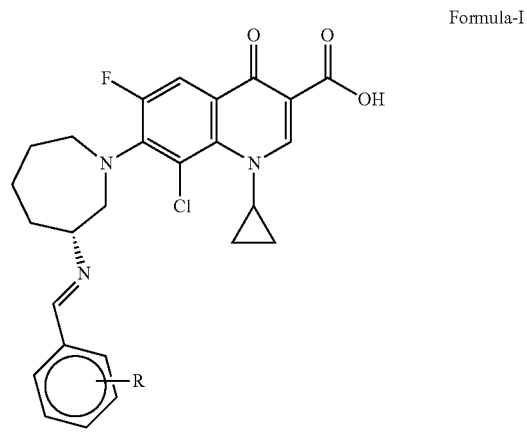

Formula-I wherein, R is hydrogen or a halogen.

2. Fluoroquinolone carboxylic acid compounds of Formula-I according to claim 1, having structural Formula-A;

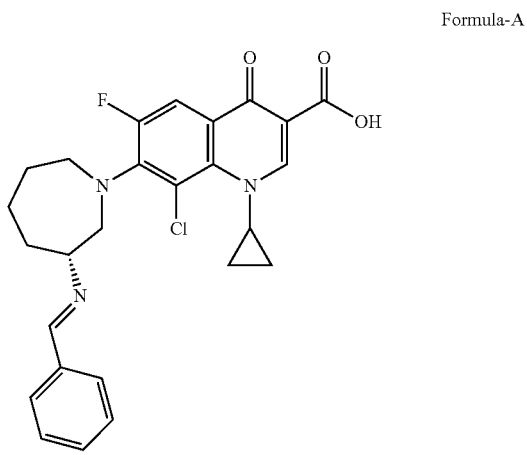 [SMILES: O=C(O)c1cn(C2CC2)c2c(Cl)c(N3CCCC[C@@H](/N=C/c4ccccc4)C3)c(F)cc2c1=O]

Formula-A and salts thereof.

3. Fluoroquinolone carboxylic acid compounds of Formula-I and salts thereof,

Formula-I

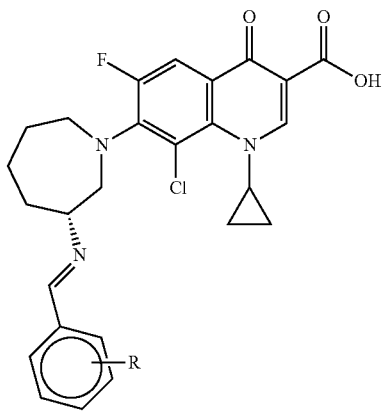

wherein said carboxylic acid compounds are selected from:

Formula-B

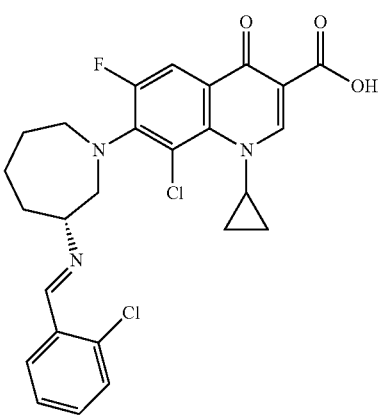

Formula-C

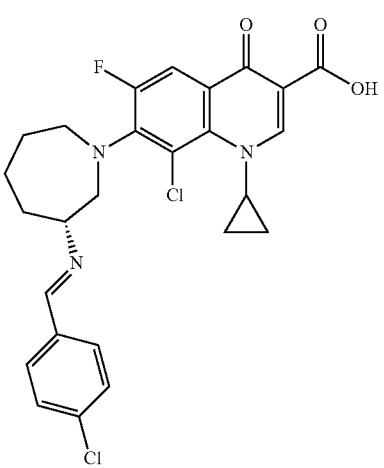

Formula-D

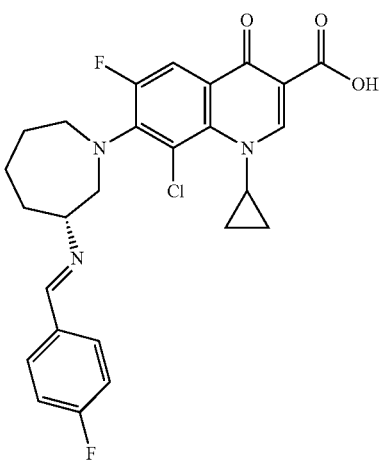

Formula-E

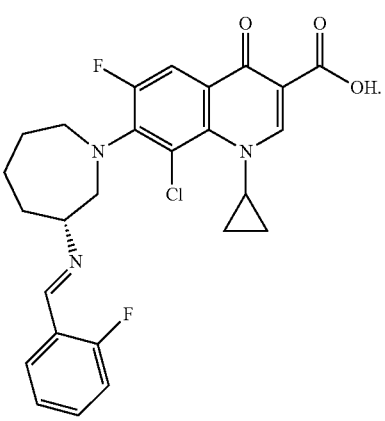

4. Fluoroquinolone carboxylic acid compounds according to claim 1, wherein said carboxylic acid compounds are R-enantiomers.

5. A process for preparation of Fluoroquinolone carboxylic acid compounds of Formula-I and salts thereof;

Formula-I

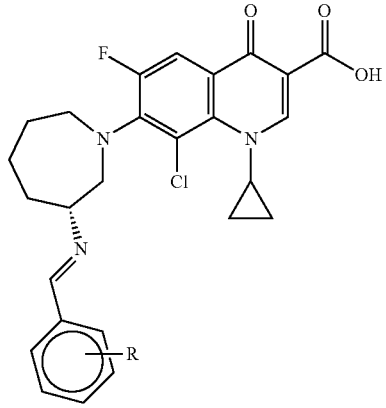

wherein, R represents hydrogen or halogen;
the process comprising:
reacting Schiff base of Formula-XIII with 8-chloro-1-cyclopropyl-6,7-difluoro-4-oxo-1,4-dihydroquinoline-3-carboxylic acid of Formula-VII;

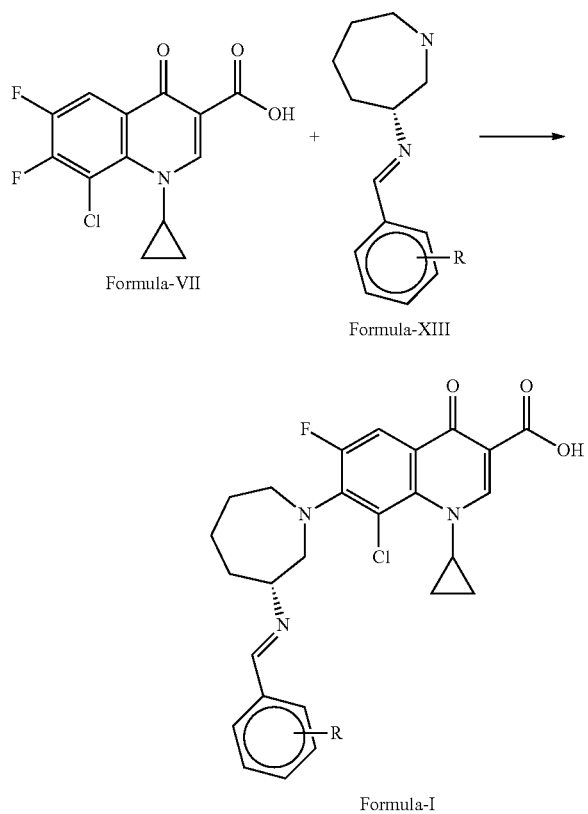

Formula-I wherein, R is hydrogen or a halogen.

6. The process according to claim 5, wherein the said Schiff base is prepared by reacting (R)-azepan-3-amine of Formula-XI with compound of Formula-XII;

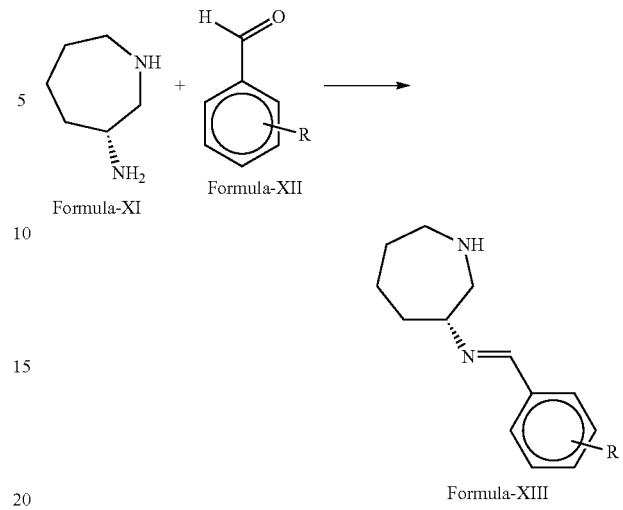

wherein, R is hydrogen or a halogen.

7. The process according to claim 6, wherein the said Schiff base is prepared in situ.

8. A process for preparation of Besifloxacin hydrochloride, comprising de-protection of fluoroquinolone carboxylic acid compounds and salts thereof, according to claim 1, in presence of aqueous hydrochloric acid to form Besifloxacin hydrochloride.

9. The process according to claim 8, wherein the fluoroquinolone carboxylic acid compounds and salts thereof are isolated in a solid state form before de-protection to Besifloxacin hydrochloride.

10. The process according to claim 8, wherein the fluoroquinolone compounds and salts thereof are in situ converted to Besifloxacin hydrochloride without isolation in a solid state form.

* * * * *